United States Patent [19]

DeVries et al.

[11] 4,335,307

[45] Jun. 15, 1982

[54] RADIOGRAPHIC APPARATUS AND METHOD WITH AUTOMATIC EXPOSURE CONTROL

[75] Inventors: Richard C. DeVries, Aurora; Edwin R. Hill, Chardon, both of Ohio

[73] Assignee: Technicare Corporation, Solon, Ohio

[21] Appl. No.: 142,187

[22] Filed: Apr. 21, 1980

[51] Int. Cl.³ .......................... G03B 41/16; N05G 1/30; A61B 6/00; H04N 5/32

[52] U.S. Cl. .............................. 250/322; 250/416 TV; 358/111

[58] Field of Search ........................ 250/416 TV, 322; 358/111

[56] References Cited

U.S. PATENT DOCUMENTS

| | | | |
|---|---|---|---|
| 3,546,461 | 12/1970 | Craig | 250/322 |
| 3,573,461 | 5/1971 | Ohlsson . | |
| 3,784,816 | 1/1974 | Abrahamsson . | |
| 3,848,130 | 11/1974 | Macovski . | |
| 4,063,092 | 12/1977 | Berdahl | 250/322 |
| 4,193,089 | 3/1980 | Brougham et al. | 358/111 |

OTHER PUBLICATIONS

Heintzen, P. H. et al., "Computer Quantitation of Angiocardiographic Images," *Non-Invasive Cardiovascular Measurements,* Sep., 1978, pp. 17–20.

"Automatic Brightness Controls of Fluoroscopic image systems," Godbarson, *Proceedings of the Society of Photo-Optical Instrumentation Engineers Medicine III* vol. 47, pp. 242–247, Aug. 1–2, 1974, CGR Instruction Handbook, SR-275p, *Service Manual, Septar Radiographic/Fluoroscopic X-ray Generator,* (preliminary) pp. 2–76 to 2–84, Jun. 1977.

*Primary Examiner*—Alfred E. Smith
*Assistant Examiner*—T. N. Grigsby

[57] ABSTRACT

A radiographic apparatus and method are disclosed for producing an x-ray shadowgraph of a patient for display on a video monitor. The apparatus includes an x-ray source for irradiating the patient and an image intensifier for receiving the radiation which has traversed the patient. The image intensifier produces an optical image of the shadowgraphic projection of the radiation through the patient. A television camera is optically connected with the image intensifier to convert the optical image into a video signal. An image processor is provided for storing and enhancing the video signals from the television camera to produce various images on the television monitor. An automatic exposure control is provided for determining the duration which the x-ray tube should be operated for properly exposing one x-ray shadowgraphic image of the patient. The exposure control includes a photoelectric transducer which is optically coupled with the image intensifier to produce a signal which is indicative of the average intensity of the optical image. An integrator integrates the intensity signal to produce a signal which is indicative of the total light exposure. When the exposure signal reaches a predetermined level, a timer which was started as the x-ray source started emitting radiation is stopped. The time indicated on the timer indicates the duration which the x-ray source should be operated to produce and properly expose one shadowgraphic image.

10 Claims, 3 Drawing Figures

RADIOGRAPHIC APPARATUS AND METHOD WITH AUTOMATIC EXPOSURE CONTROL

BACKGROUND OF THE INVENTION

This invention pertains to the radiographic arts and more particularly to automatic exposure controls for radiographic diagnostic apparatus. The invention is particularly applicable to radiographic apparatus for producing video encoded shadowgraphs of a region of the patient. More specifically, it is applicable to an apparatus which processes a plurality of video encoded shadowgraphs by superimposition and other mathematical techniques to produce electronically enhanced video shadowgraphic images of a patient. It will be appreciated, however, that the invention has broader applications in other radiographic apparatus which produce an intermediate optical image.

In the past, others have devised radiographic apparatus for producing shadowgraphs which are displayed on a video monitor. Some of these systems are shown by way of example in U.S. Pat. No. 3,573,461, issued Apr. 6, 1971 to S. A. Ohlsson, U.S. Pat. No. 3,784,816, issued Jan. 8, 1974 to S. Abrahamsson, or U.S. Pat. No. 3,848,130, issued Nov. 12, 1974 to A. Macovski. Such systems consist of an x-ray source for irradiating the patient or other object to be examined and a fluorescent screen for converting the x-radiation into an optical image. A television camera which is disposed to view the optical image produces a video representation of the image. The video representations are manipulated by a computer or processor and displayed on a video monitor.

To produce a good video image, the television camera must receive sufficient light from the optical image to produce good contrast, but no so much light that the image is washed out. Further, it is undesirable to irradiate the patient with radiation for a longer duration than is necessary or with a higher intensity than is necessary. Three factors have been varied to obtain a properly exposed video image—adjusting the KV of the power supply which determines the penetrating power of the x-rays, adjusting the milliamperes (Ma) of the power supply which determines the intensity of the x-rays, and adjusting the duration that the x-ray source is actuated. These determine the brightness of the optical image and the duration which the optical image is available for the television camera to monitor.

The intensity of the x-rays reaching the fluorescent screen, is greatly effected by the thickness and density of the patient or object through which the radiation has traversed. Small variations in the thickness, density, or other radiation absorptive properties of the patient produce relatively large differences in the intensity of radiation reaching the fluorescent screen. Accordingly, each time a new patient or different part of the same patient is to be examined, it is necessary to redetermine the optimum exposure. In the past the optimum exposure was determined by trial and error. That is, the operator would adjust the milliamperes and the duration and possibly the KV to values which he felt would produce a good image. After examining the produced image, the operator would readjust milliamperes or duration to improve the quality of the image produced. This trial and error procedure would often result in x-raying the patient a half a dozen times merely to calibrate the exposure without producing usable data. The radiation exposure of the patient during calibration is undesirable and excessive.

SUMMARY OF THE INVENTION

We have discovered a new and improved radiographic apparatus with an automatic exposure system which overcomes the above problems and others. It provides an automatic exposure system in conjunction with the radiographic apparatus for minimizing a patient's exposure to radiation.

In accordance with the present invention, there is provided a radiographic apparatus which comprises a radiation source, a radiation to optical image conversion means for converting the radiation from the radiation source to an optical image, a television camera disposed to view the optical image of the radiation to optical image conversion means, and an automatic exposure system. The automatic exposure system includes a photoelectric transducer which monitors the light from at least a part of the optical image and produces an intensity signal which varies with the intensity received. An integrator integrates the intensity signal with respect to time to produce a signal indicative of the light exposure. When the exposure signal reaches a predetermined level, the radiation source is stopped from emitting radiation. Alternately, a timing means times the duration from commensing to irradiate the patient until the integration signal reaches the predetermined level. This timed duration is used for subsequent examinations of the examined object. In this manner the relative gray scales of subsequent exposures are comparable.

The principle object of the invention is to minimize the radiation dosage received by a patient or other examined object.

Another object of the invention is to produce video shadowgraphic images which are exposed consistently with each other.

DESCRIPTION OF THE PREFERRED EMBODIMENT

Figure 1:
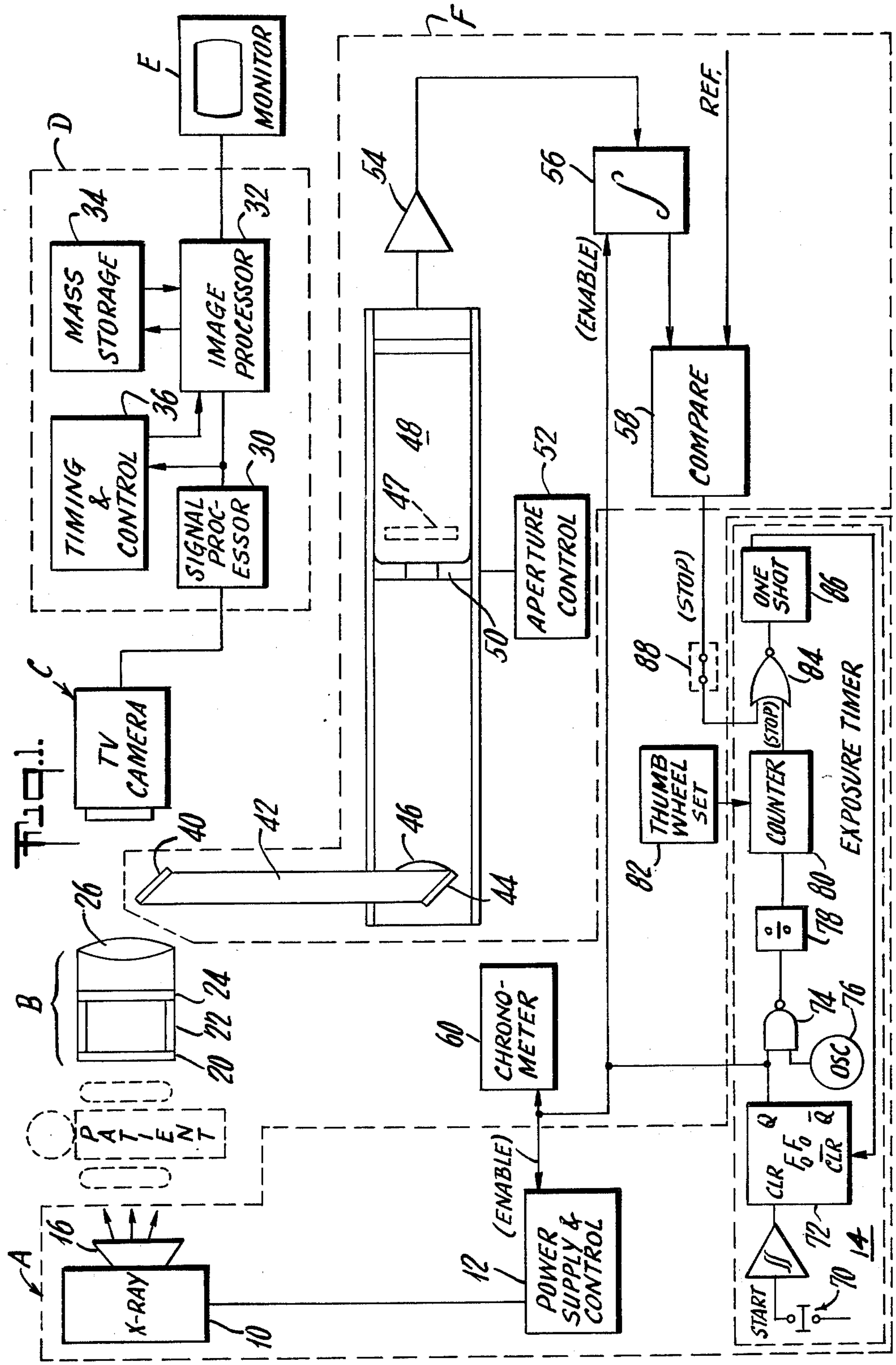
FIG. 1 is a schematic diagram of a radiographic apparatus in accordance with the present invention.

With reference to FIG. 1, a penetrating radiation source A generates penetrating radiation for irradiating the object to be examined. A radiation to optical image conversion means such as an image intensifier B converts the radiation into an optical image. More specifically it converts the two dimensional shadow or attenuation in the radiation intensity which is caused by traversing the three dimensional examined object, into an optical image or shadowgraph. A television camera C converts the optical image from the radiation to optical image conversion means B into a video signal. A video processing means or video processor D processes the video signal to perform various predetermined manipulations on the signal to produce video images with greater medical significance. A video monitor E is provided for displaying the video images of the shadowgraphs. An exposure control means F determines the duration for which x-ray source A should be actuated to produce a properly exposed image without irradiating the examined object unnecessarily.

The radiation source A comprises an x-ray tube 10 for generating x-radiation. The invention contemplates substituting other types of penetrating radiation for x-rays. Connected with x-ray tube 10 is a power supply and control circuit or means 12 for actuating the x-ray source. The control circuit 12 includes a power supply for operating the x-ray tube at selectable perameters. Specifically it provides for adjusting the KV and the milliamperes (Ma) which are supplied to the x-ray tube when it is actuated. An adjustable exposure timer 14 controls the duration which the control means 12 enables the x-ray source to emit x-rays. The adjustable exposure timer is adjustable between generally one and about a hundred milliseconds. An adjustable collimator 16 is disposed adjacent the x-ray tube for selecting the size and shape of the beam of radiation emitted from the x-ray source. The collimator allows the operator to irradiate only that region or area of the patient which is of interest.

Although the x-ray to optical radiation conversion means in the preferred embodiment is a conventional image intensifier, the invention contemplates other structures which convert radiation to corresponding optical images. The image intensifier B has an input screen 20 which frees electrons in response to being irradiated. The rate at which electrons are freed at any point varies with the intensity of received radiation. Electron accelerating means 22 are provided for accelerating the electrons released by screen 20 toward a phosphorescent or fluorescent screen 24. Upon being struck by the electrons, screen 24 produces light. The intensity of light at any point on the screen 24 is determined by the intensity of impinging electrons. Thus screen 24 produces an optical image whose intensity at any point varies with the intensity of radiation received on screen 20. Disposed adjacent the screen 24 is a lens 26. Lens 26 is selected so that the image on screen 24 is focused at infinity. That is, light rays originating at screen 24 exit lens 26 as parallel rays. The television camera C is a conventional and commonly available lead oxide (PbO) target television camera or vidicon. The television camera is disposed within the vignetting cone of lens 26 to view the entire optical image.

The video processor D may include a signal processor 30 for processing on the gray scale portion of the video signal to improve the image. One function which the signal processor 30 may perform on the gray scale, is a logarithmic compression of its amplitude. An image processor 32 receives the video signals from the signal processor 30 and stores one or more video frames from the television camera. The image processor 32 operates on the stored frames in various ways, such as by subtracting the corresponding pixels of two frames to determine the difference in the two frames. The operation and function of the image processor 32 is explained in further detail below in conjunction with FIG. 3. A mass storage means 34, such as a video tape or disc system, is provided to store a multiplicity of frames of video data. A timing and control circuit or means 36 controls the timing with which the image processor handles the video data. The video monitor E is a conventionally available television or other video monitor.

The automatic exposure means F includes an image splitting means 40 disposed in the vignetting cone of the lens 26 for splitting the optical image from the image intensifier B between the television camera C and the exposure control means F. It will be appreciated that the parallel rays of light produced by the focus at infinity lens 26 enables the television camera C and the exposure control means F both to view the entire optical image on screen 24. In the preferred embodiment, the optical image splitting means 40 is a first surface mirror which is disposed within the vignetting cone of the lens 26. A Plexiglas resin light guide 42 channels the optical image reflected by mirror 40 to a second first surface mirror 44. Mirrors 40 and 44 and light guide 42 comprise means for receiving the entire optical image from the image intensifier. Alternately, the receiving means may be other structures, such as a partially reflective mirror, for receiving the optical image. Adjacent the second mirror 44 is a second lens 46 or similar means for focusing the image on the light sensitive region 47 of a photoelectric transducer 48. The lens 46 is attached to the light guide 42. Specific to the preferred embodiment, the lens 46 focuses the image on the target cathode of a photomultiplier tube. An adjustable aperture 50 blocks a part of the optical image from being received by the photoelectric transducer 48. By adjusting the size and position of the aperture, one can select the area of the optical image which is to control the exposure. Generally, the area of the optical image which is selected is the area of primary medical interest. The area is selected to be sufficiently large that it is representative of the intensity of light from the part of the image which is primary interest. The aperture may restrict the light sensitive region 47 to receive a circular part of the image in the geographic center of the optical image with a diameter which is about one half of the total width of the image produces satisfactory results. If the photoelectric transducer 48 monitors a part of the optical image which is shielded from radiation by the collimating means 16, the average intensity in the area monitored will be erroneously low due to the dark area caused by collimating means 16. An automatic aperture control 52 is provided to adjust the size or position of aperture 50.

The photoelectric transducer 48 produces an electrical signal whose amplitude varies as the average intensity of light which is received on its light sensitive region. A transimpedance amplifier 54 converts the intensity signal from an analog current signal to an analog voltage signal. The transimpedance amplifier 54 is explained below in further detail in conjunction with FIG. 2. The intensity signal is integrated with respect to time by an integrator 56. An integration of intensity with respect to time provides an indication of the exposure. The integrator 56 is reset before the x-ray source is actuated. Accordingly, the output of integrator 56 is an exposure signal which varies as the total exposure since the actuation of the x-ray source. The integrating means 56 is explained in greater detail below in conjunction with FIG. 3. A comparing means 58, e.g., LM-311, compares the exposure signal from integrating means 56 with a reference signal. The reference signal is selected during the initial calibration of the apparatus with an exposure value which has previously produced an optimum video image with the specific television camera C and video processor D. When the integration signal matches the reference signal, comparator 58 produces a stop signal.

The stop signal causes the x-ray control circuit 12 to stop the x-ray source from emitting x-radiation. The comparator also causes a chronometer 60 or similar timing means to indicate the duration between the actuation of the x-ray source and the integrator attaining the reference amplitude.

The exposure timer 14 comprises a start switch 70 which initiates an x-ray exposure. The start switch causes a flip flop, 72, e.g., 74LS74, to start an enable pulse by producing a high output. The enable pulse enables an AND gate 74 to pass the pulses from an oscillator 76. A frequency divider 78 reduces the oscillator frequency to 10 kilohertz. This provides an 0.1 millisecond minimum timing interval. A counter 80, e.g. LS192, is indexed to count down at 0.1 millisecond intervals. When the counter 80 counts down to zero, it generates a stop signal. The initial count, i.e. exposure time, is set by the operator on a thumb wheel switch 82. The stop signal from the comparator 58 and the counter 80 are received by an OR gate 84. The first stop signal received by the OR gate actuates a one shot 86, e.g. LS221. The one shot 86 produces a pulse of the appropriate amplitude and duration to reset the flip flop 72. Resetting the flip flop 72 terminates the enable signal causing the x-ray source to stop emitting x-radiation. The chronometer is connected with the flip flop 72 for timing the duration of the enable pulse. A suitable chronometer is an Intersil, Inc., ICM7227. Thus if the thumb wheel switch sets a longer time duration than the time to reach the preselected exposure level, this chronometer 60 indicates the appropriate exposure duration to be set on thumb wheel switch. A switch 88 is provided for disconnecting the automatic exposure means F from the x-ray source A.

In the preferred embodiment, the radiographic system is used to produce a first or mask video image of an x-ray shadowgraph of a region of a patient. A relatively small amount of an x-ray opaque contrast agent is injected into the patient. A second or post contrast video image of the x-ray shadowgraph of the same region of the patient after the injection is produced. The image processor 32 subtractively combines these two images to produce a differential image indicative of the effect on x-ray absorption caused by the opaque contrast agent. To perform an accurate subtraction, it is desirable to have the exposure the same for both images. This is true even though the opaque contrasting agent generally lowers the intensity of the second image. This keeps the exposure of those parts of the images which is not attributable to the opaque contrasting agent the same. The adjustable exposure timer 14 is adjusted to cause the x-ray source to emit x-rays for the same duration to produce both images. If the apparatus is not to be used in a mode in which the video images are to be compared, the stop signal from comparator 58 may be used to stop the actuation of the x-ray source for each exposure. In this exposure controlled mode, it is still desirable to set adjustable exposure timer 14 to provide a failsafe shutoff after a reasonable duration. Because the time required for a conventional television camera to sweep one frame is about sixteen milliseconds, it is desirable to adjust the milliamperes supplied to the x-ray tube such that the actuation duration or exposure time is about sixteen milliseconds. This enables each frame produced by the television camera to produce one video image. If a longer duration is required to make a good image, two or more video frames are combined in the image processor 32 to produce a composite video image.

Figure 2:
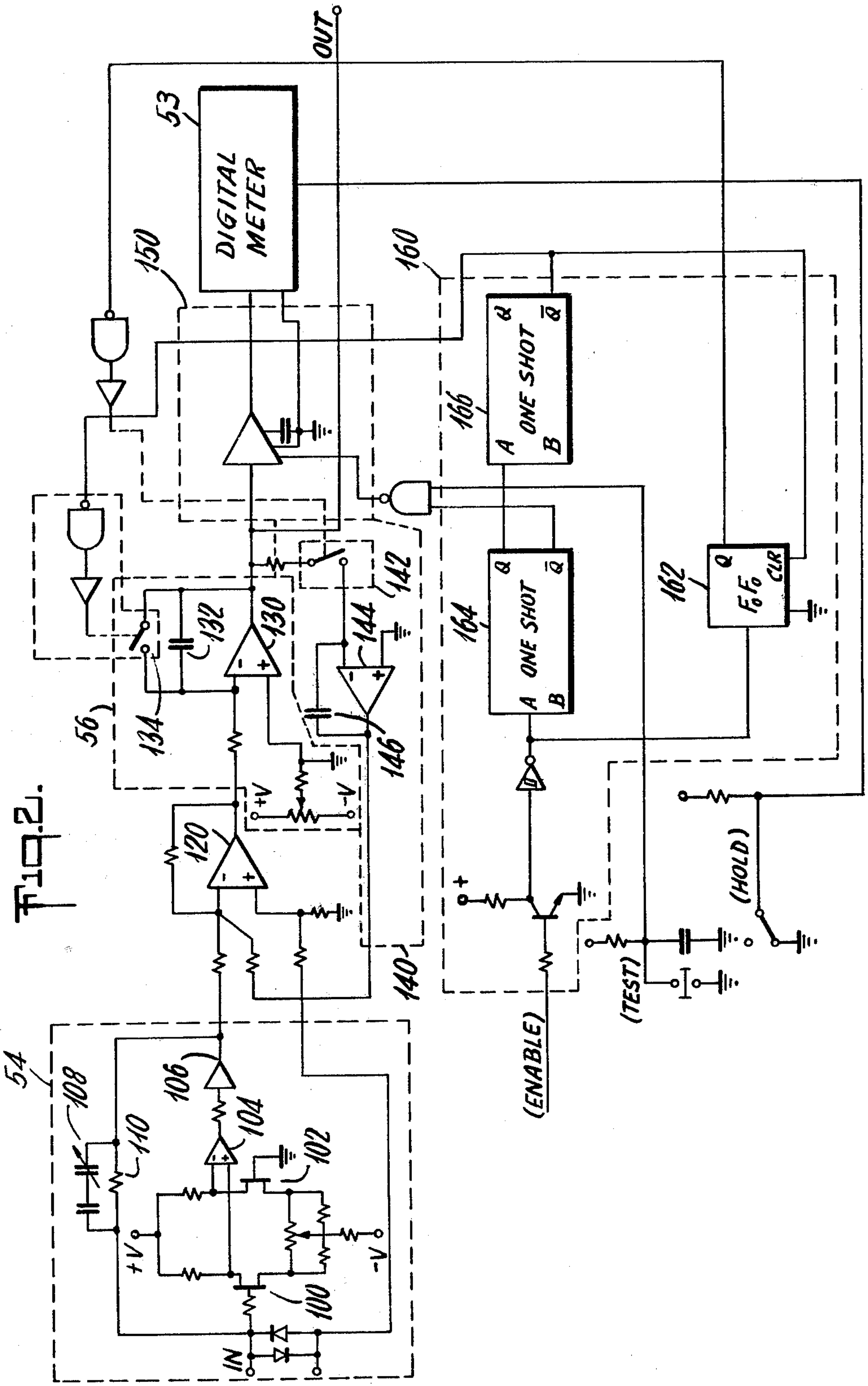
FIG. 2 is a detailed schematic diagram of the transimpedance amplifier and of the integration means of FIG. 1.

With reference now to FIG. 2, the transimpedance amplifier 54 comprises a pair of matched monolithic dual J-FET's 100 and 102 which are interconnected as a differential current amplifier. Each J-FET is connected in series with a resistor to produce a voltage across the resistor. A suitable component is a 2N5564. The J-FET's 100 and 102 are connected with a differential amplifier means 104, e.g., an LF356. The differential amplifier means 104 subtractively combines the signals to produce an output which is related to the difference between the signals received by J-FET 100 and J-FET 102. A unity gain buffer amplifier 106, e.g. an LH0002, provides an increased output current drive. A feedback loop comprising a capacitance 108 and resistance 110 connects the output of buffer amplifier 106 with the input to the transimpedance amplifier 54. The feedback loop forms a virtual ground at the input to the transimpedance amplifier means.

With continued reference to FIG. 2, the intensity signal in the form of an analog voltage from transimpedance amplifier 54 is received by a buffer amplifier 120, e.g., an LF356. The buffered intensity signal is received by the integrator 56. Integrator 56 includes a differential amplifier 130, e.g., an LF356. The intensity signal forms one input to differential amplifier 130. The other input to differential amplifier 130 is an offset voltage provided by an initial manual calibration. Connected between the output and one of the inputs of the differential amplifier 130 is a charge storage device or capacitor 132, such as an 0.1 microfarad capacitor. The intensity signal causes a charge buildup on the capacitor 132. As the charge builds on capacitor 132, the input to the differential amplifier 130 increases. In this manner, the output is an integration of the input with respect to time. A reset switch 134 is provided for removing the charge from capacitor 132 to reset integrator 56. Alternately other integrators, such as a voltage to frequency converter coupled with a counter, may be used.

An automatic zero circuit 140 is provided for supplying an automatically adjusted offset signal to the input of the integrator 56. When the x-ray source A is not actuated, a switching device 142 is closed. This causes any nonzero exposure signal from the output of the integrator 56 to be conveyed to a self adjusting offset bias signal generating means for generating a bias signal which tends to zero the output of the integrator 56. In the preferred embodiment, the self adjusting offset signal generator comprises a differential amplifier 144, such as an LF356, and a charge storage device or capacitor 146, such as an 0.01 microfarad capacitor. The output of amplifier 144 is applied to the input of the integrator 56. The output of amplifier 144 is of the opposite sign as the signal which is received through switch 142. The output of operational amplifier 144 acts to reduce the signal received through switch 142, until the received signal is brought to substantially a zero magnitude. As long as switch 142 is closed, operational amplifier 144 adjusts to produce the analog voltage needed to produce a zero output from amplifier 130. When switch 142 is opened, capacitor 146 causes operational amplifier 144 to continue to produce the same output for a duration which is at least as long as the duration of the exposure of one image.

The exposure signal from amplifier 130 is received by a sample and hold circuit 150 which comprises an LF398 and a 0.1 microfarad capacitor. The sample and hold circuit samples and holds for a short duration the analog exposure signal. A digital meter 53, e.g., a Datel DM-4100L, provides a digital display of the analog value in the sample and hold circuit 150. In this manner, the digital meter 53 provides a display of the amplitude of the exposure signal from the integrator 56.

The enable signal from the adjustable exposure timer 14 is received by a logic circuit 160. The rising edge of the enable pulse causes a flip flop 162, e.g. LS74, to open switch 142. The falling edge of the enable pulse causes a one shot 164. e.g. LS221, to enable the sample and hold 150 to monitor the final integration voltage, i.e. exposure level. The one shot 164 also triggers a second one shot 166, e.g. LS221. After a very short delay, the one shot 166 resets the flip flop 162 causing switch 142 to be closed and closes switch 132 to reset the integrator 56.

Figure 3:
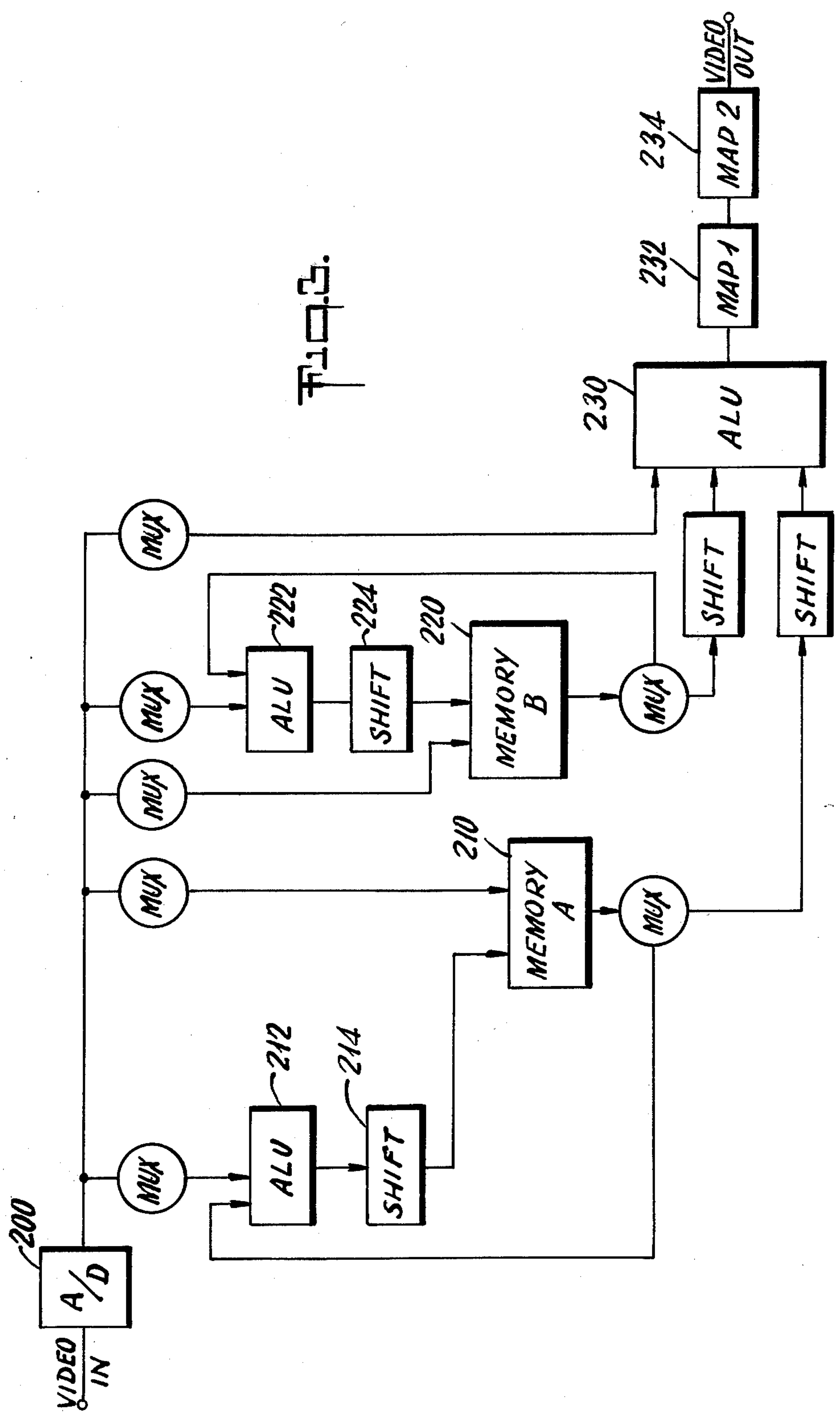
FIG. 3 is a schematic diagram of a preferred embodiment of the image processor of FIG. 1.

With reference now to FIG. 3, a suitable image processor is disclosed in copending application Ser. No. 138,400 of Robert H. McCarthy, filed Apr. 8, 1980, entitled "Dynamic Image Enhancement Method and Apparatus Therefore" which is assigned to the assignee of the present application. The image processor 32 provides dynamic image enhancement with digital subtraction and other processing of images. The apparatus is designed to produce a mask or precontrast image, i.e., the shadowgraphic image through a preselected area or region of interest of a patient without an opaque contrasting medium introduced into the preselected area. The system is also designed to produce a post contrast image, i.e., the shadowgraphic image through the same preselected area of the patient with an opaque contrasting agent introduced into the preselected area. The mask image and the post contrast image are each a single video frame from the television camera. Alternately the mask and post contrast images may be the composite of a plurality of frames from the television camera. The system is designed to subtract the mask image and the post composite contrast image to produce a differential image for display on the video monitor E. The video processor 32 comprises an analog to digital converter 200 for converting the analog gray scale portion of the video signals to corresponding digital signals. The video signal of the mask image is conveyed by a multiplexing means to a first memory 210. Memory 210 is a 256×256 pixel matrix array with 8 bits of resolution. It stores 256 eight bit bytes of digital gray scale data in each of the 256 lines which comprise one video frame. If the image is to be the composite of two or more frames, the video data from a subsequent frame is conveyed by multiplexing means to an arithmetic logic unit 212. The arithmetic logic unit 212 combines each byte of the video signal with the corresponding byte of video data stored in the corresponding pixel of the first memory 210. A shift means 214 divides the amplitude of each byte of the sum from arithmetic logic unit 212 in half by dropping the least significant bit. This average is returned to the corresponding pixel of memory 210. Subsequent similar averaging processes may be performed, if the image is to be a composite of more than two frames.

A relatively small amount of an x-ray opaque contrast agent is injected into the vein of the patient. After about ten to fifteen seconds, the contrast agent is carried by the blood into the area being examined with the radiographic apparatus. After the x-ray opaque contrast agent has entered the area of interest, a post contrast image is produced for storage in a second memory 220. The video signal from the television camera C is converted from analog to digital by the analog to digital converter 200 and conveyed by multiplexing means to the second memory 220. The second memory 220 is again a 256×256 pixel array with 8 bits of resolution. If the post composite contrast image is to be a composite of several frames, an arithmetic logic unit 222 and a shift means 224 are provided for averaging the plurality of frames which comprise the composite post contrast image. If a plurality of post contrast images or mask images are to be produced, memories 210 and 220 may be connected with the mass storage device 34 to transfer each completed image for storage.

To subtract the mask image from the post contrast image, an arithmetic logic unit 230 is provided. The arithmetic logic unit 230 subtractively combines the corresponding pixels from each of the first and second memories 210 and 220. The output of arithmetic logic unit 230 is the differential image. Alternately, by appropriate actuation of the multiplexing means, the arithmetic logic unit 230 may receive and cause to be displayed, the image stored in memory 210, the image stored in memory 220, or the real time image from the television camera C.

A mapping memory 232 is provided to perform image enhancement. Mapping memory 232 is a 256×8 memory array which reduces the $2^8$ amplitudes that can be stored in memories 210 and 220 to one of approximately 32 gray scales for display on the video monitor. A second mapping memory 234 is provided for gray level mapping. Mapping memory 234 provides a gray scale distribution for calibration functions.

The timing and control circuit 36 receives the synchronization information of the video signal. It uses the synchronization information to address memories 210 and 220 in such a manner that the incoming gray scale data are stored in the appropriate pixel of each memory. The timing and control circuit 36 further controls the multiplexing means such that each frame of gray scale information is conveyed along the appropriate path of the image processor circuitry. The multiplexing means may also connect the analog to digital converter 200, memory 210, and memory 220 with the mass storage device 34. Under control of timing and control circuitry 36, incoming frames from the television camera, mask images, composite mask images, post contrast images, composite post contrast images, and difference images may be stored in the mass storage device and be retrieved for display or reprocessing in the image processing means 32.

We claim:

1. A method of reducing a patient's exposure to x-radiation in a radiographic diagnostic apparatus comprising the steps of:

(a) irradiating a region of the patient with x-radiation to generate a shadowgraphic projection through the region;

(b) converting the x-radiation which has traversed the region to an optical image of the shadowgraphic projection;

(c) converting the optical image to a video signal of the shadowgraphic projection;

(d) determining the average intensity of light over at least a part of the optical image;

(e) integrating the intensity with respect to time to determine the exposure to light since the beginning of the integration;

(f) when the exposure reaches a predetermined level, stopping the irradiation of said region with x-radiation;

and (g) determining the exposure time between the commencing of irradiating the region with x-radiation and the exposure reaching the predetermined level.

2. The method as set forth in claim 1 further comprising the steps of digitizing and storing the video signal of the shadowgraphic projection.

3. The method as set forth in claim 2 further comprising the steps of:

(a) injecting the patient with an x-ray opaque contrast agent;

(b) irradiating said region with x-radiation for said exposure time to generate a shadowgraphic projection through the region and injected x-ray opaque contrast agent;

(c) converting the x-radiation which has traversed the region injected with x-ray opaque contrast agent to a second optical image;

(d) converting the second optical image to a second video signal;

(e) digitizing and storing said second video signal; and (f) digitally subtracting said first and second video signals to form a differential video signal which represents a differential image that is the difference of the first and second images.

4. The method as set forth in claim 3 further comprising the step of converting said differential video signal to a visual display of said differential image.

5. A radiographic apparatus for converting x-ray shadowgraphs to video signals for display on a video monitor or the like, which comprises:

(a) an x-ray source for irradiating an examined object with x-radiation to generate x-ray shadowgraphs thereof;

(b) a radiation converting means for converting received x-radiation to an optical image, the radiation converting means being disposed to receive from said x-ray source x-radiation which has traversed the examined object;

(c) a television camera for converting the optical image to a video signal, said television camera being optically connected with said radiation to optical image converting means to convert the optical image into said video signal;

(d) receiving means for receiving substantially the entire optical image from said radiation converting means;

(e) a photoelectric transducer being optically connected with said receiving means for converting at least a part of the received optical image to an electrical intensity signal which varies generally with the intensity of light from at least the part of the optical image;

(f) integration means for integrating the intensity signal to produce an integration exposure signal, said integration means being operatively connected with said photoelectric transducer;

(g) timing means for timing a duration between activation of said x-ray source and the time when the exposure signal reaches a predetermined exposure level; and (h) comparing means for comparing the amplitude of said exposure signal with a reference signal indicative of said predetermined exposure level, said comparing means producing a stop signal when said exposure signal reaches reference relationship with the predetermined signal, said comparing means being operatively connected with said integrating means to receive the exposure signal therefrom and being operatively connected with said timing means to stop the timing means with said stop signal.

6. The radiographic apparatus as set forth in claim 5 wherein said comparing means is operatively connected with said x-ray source for stopping said x-ray source from emitting radiation in response to said stop signal, such that the x-ray source irradiates the examined object with radiation only for the duration necessary to reach the predetermined exposure level.

7. A radiographic apparatus for converting x-ray shadowgraphs to video signals for display on a video monitor or the like, which comprises:

(a) an x-ray source for irradiating an examined object with x-radiation to generate x-ray shadowgraphs thereof;

(b) a radiation converting means for converting received x-radiation to an optical image, the radiation converting means being disposed to receive from said x-ray source x-radiation which has traversed the examined object;

(c) a television camera for converting the optical image to a video signal, said television camera being optically connected with said radiation to optical image converting means to convert the optical image into said video signal;

(d) receiving means for receiving substantially the entire optical image from said radiation converting means;

(e) a photoelectric transducer being optically connected with said receiving means for converting at least a part of the received optical image to an electrical intensity signal which varies generally with the intensity of light from at least the part of the optical image;

(f) integration means for integrating the intensity signal to produce an integration exposure signal, said integration means being operatively connected with said photoelectric transducer;

(g) timing means for timing a duration between activation of said x-ray source and the time when the exposure signal reaches a predetermined exposure level; and (h) automatic zero means for applying a bias signal to the input of said integration means which bias signal tends to zero the output of said integration means when the radiation source is not actuated, the automatic zero means comprising switching means for switching the output of said integration means to the automatic zero means when the x-ray source is not actuated, self-adjusting bias-signal-generating means for generating a bias signal which tends to zero the output of said integration means, said self-adjusting bias-signal-generating means being connected with the input of said integration means, such that when the x-ray source is not actuated the self-adjusting bias-signal-generating means adjusts the bias signal and when the x-ray source is actuated continues to generate the adjusted bias signal.

8. The radiographic apparatus as set forth in claim 7 further comprising a transimpedance amplifier means disposed between said photoelectric transducer and said integrating means, said transimpedance amplifier means comprising an FET differential current amplifier means for applying a current across a pair of resistances, and a second differential amplifier means for differentially amplifying the output of the FET differential current amplifier means.

9. The radiographic apparatus as set forth in claim 8 wherein said transimpedance amplifier means further comprises a feedback loop for holding the input potential of said FET differential current amplifier to a virtual ground.

10. A radiographic diagnostic apparatus for producing video displays of x-ray shadowgraphs of an examined region of a patient with a minimal exposure of the patient to radiation, the apparatus comprising:

(a) an x-ray source for emitting x-radiation for generating an x-ray shadowgraphic projection through the examined region, said x-ray source including control means for starting and stopping the emission of x-radiation by the x-ray source;

(b) a radiation converting means for converting said x-ray shadowgraphic projection to an optical shadowgraphic image, said radiation converting means comprising a screen for displaying said optical image and a lens for focusing light rays from the optical image along substantially parallel paths to focus the optical image at infinity;

(c) a television camera for converting said optical image to a video signal representing the x-ray shadowgraphs, said television camera being disposed to view said optical image through said focus at infinity lens;

(d) image processing means for processing said video signal to enhance the x-ray shadowgraph, said image processing means being operatively connected with said television camera means;

(e) a video monitor for converting said video signals to said video display of the shadowgraphs;

(f) a photoelectric transducer for producing an output intensity signal which varies with the intensity of light received on its light sensitive region;

(g) image splitting means for splitting the parallel light rays from the focus at infinity lens to cause said television camera to receive substantially the complete optical image and causing substantially the complete optical image to be focused on the light sensitive region of said photoelectric transducer;

(h) an adjustable aperture means for selectively blocking the light sensitive region of the photoelectric transducer from receiving a part of the substantially complete optical image from said image splitting means;

(i) integration means for integrating the output intensity signal from said photoelectric transducer to produce an integration exposure signal which varies with the cumulative light exposure of the light sensitive region during the integration;

(j) comparing means for comparing the integration exposure signal with a preselected reference signal to produce a stop signal when a predetermined relationship between the integration exposure signal and the preselected reference signal is reached, said comparing means being operatively connected with said control means of the x-ray source, said stop signal causing said control means to stop the x-ray source from emitting x-radiation;

and (k) timing means for timing the time period between the x-ray sources start of emitting x-rays and integration exposure signal reaching the predetermined relationship with the preselected reference signal, said timing means being operatively connected with said control means to be started thereby and operatively connected with said comparing means to be stopped in response thereto.

* * * * *